United States Patent
Negre et al.

(10) Patent No.: US 8,733,394 B2
(45) Date of Patent: *May 27, 2014

(54) DEVICE AND METHOD FOR MECHANICALLY LOCATING AND READING THE SETTING OF AN ADJUSTABLE VALVE

(75) Inventors: Philippe Negre, Paris (FR); Christophe Moureaux, Besançon (FR); Jean-Philippe Lemaitre, Rochefort (FR)

(73) Assignee: Sophysa, Orsay Cedex (FR)

( * ) Notice: Subject to any disclaimer, the term of this patent is extended or adjusted under 35 U.S.C. 154(b) by 1109 days.

This patent is subject to a terminal disclaimer.

(21) Appl. No.: 12/677,171

(22) PCT Filed: Sep. 10, 2007

(86) PCT No.: PCT/IB2007/003448
§ 371 (c)(1),
(2), (4) Date: Nov. 5, 2010

(87) PCT Pub. No.: WO2009/034410
PCT Pub. Date: Mar. 19, 2009

(65) Prior Publication Data
US 2011/0048539 A1    Mar. 3, 2011

(51) Int. Cl.
*A61M 27/00* (2006.01)
*F16K 37/00* (2006.01)
(52) U.S. Cl.
USPC ........ 137/554; 137/551; 33/355 R; 33/355 D; 33/DIG. 1; 251/65; 604/9
(58) Field of Classification Search
USPC ............... 137/551, 554; 251/65; 33/349, 352, 33/354, 355 R, 355 D, DIG. 1; 604/9
See application file for complete search history.

(56) References Cited

U.S. PATENT DOCUMENTS 3,881,258 A    5/1975    Iddings
4,608,992 A *  9/1986    Hakim et al. ............... 600/431
(Continued)

FOREIGN PATENT DOCUMENTS

FR    2861569 A1    5/2005
WO    00/54826 A1   9/2000

OTHER PUBLICATIONS

Smith, Ralph J. Circuits, Devices and Systems A First Course in Electrical Engineering, N.Y., John Wiley & Sons, 1976, p. 550-551. ISBN 0-471-80171-2.*

*Primary Examiner* — John Rivell
(74) *Attorney, Agent, or Firm* — Clark & Brody

(57) ABSTRACT

A device for mechanically locating and reading the setting of an adjustable magnetic valve for controlling the flow of a fluid in a predetermined direction (D) comprises a magnetic compass (10) and a selector (20) provided with an alignment mark (21) for aligning the magnetic compass (10) with respect to the direction (D) in which the fluid flows through the valve (V). The compass (10) comprises a reference plane and a magnetic indicator (12) which is mounted such that it can pivot in all three dimensions of space under the effect of the magnetic field of the valve, the valve setting being represented by the angle (β) formed, in the reference plane, between the magnetic indicator (12) and the alignment mark (21) when the magnetic indicator (12) is positioned perpendicular to the reference plane, the magnetic compass then being centered on the magnetic center of the valve.

19 Claims, 3 Drawing Sheets

(56) References Cited

U.S. PATENT DOCUMENTS

| | | |
|---|---|---|
| 4,676,772 A | 6/1987 | Hooven |
| 6,094,830 A * | 8/2000 | Gloor et al. ................. 33/355 R |
| 6,366,073 B1 * | 4/2002 | Shiao .............................. 324/67 |
| 6,385,133 B1 * | 5/2002 | Miyauchi .................... 33/355 R |
| 7,921,571 B2 * | 4/2011 | Moureaux et al. .......... 33/355 R |
| 2005/0096579 A1 * | 5/2005 | Bertrand et al. ................... 604/9 |
| 2005/0120571 A1 | 6/2005 | Moskowitz et al. |
| 2006/0062641 A1 * | 3/2006 | Rivers et al. .................. 408/1 R |

\* cited by examiner

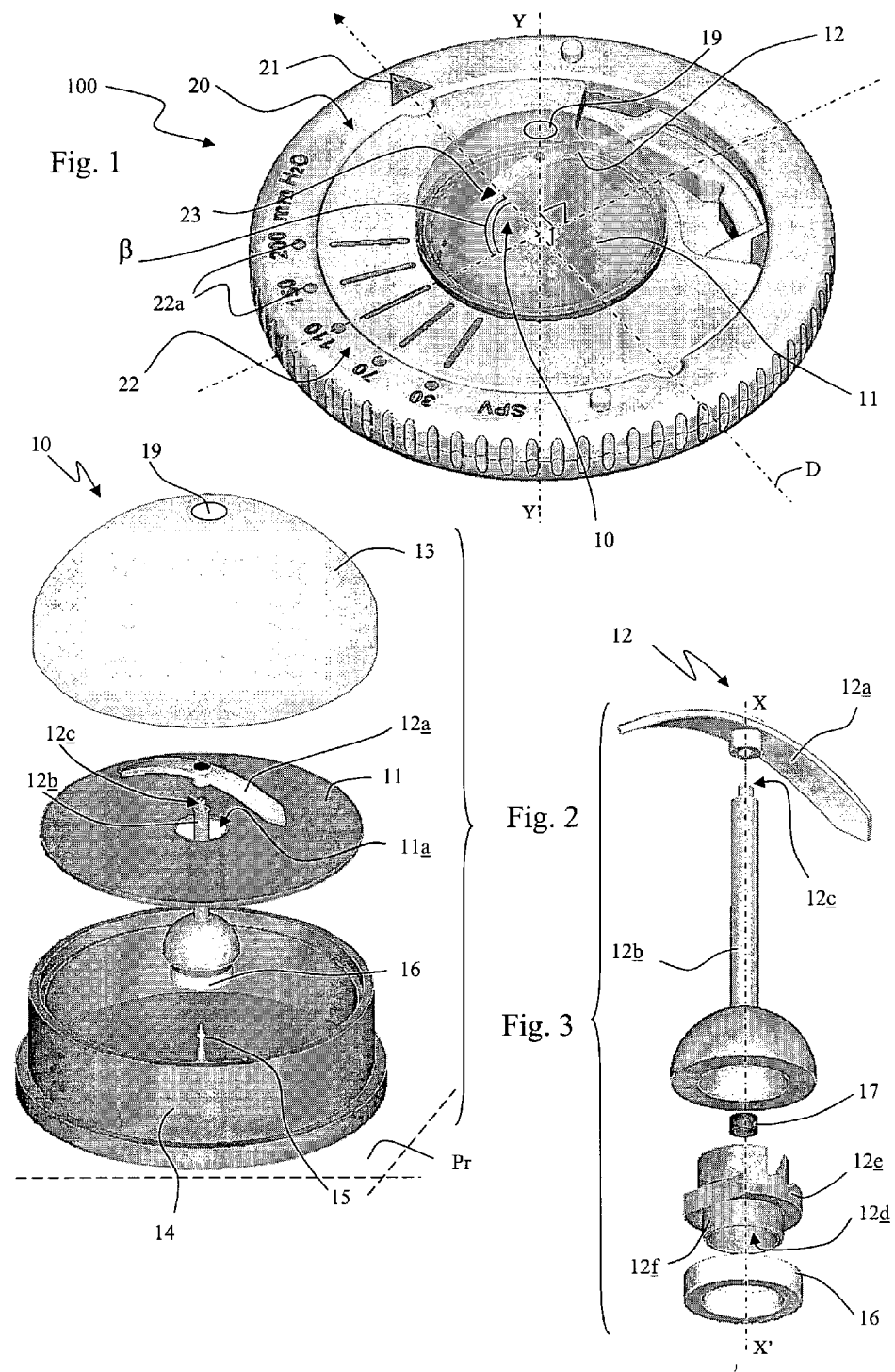

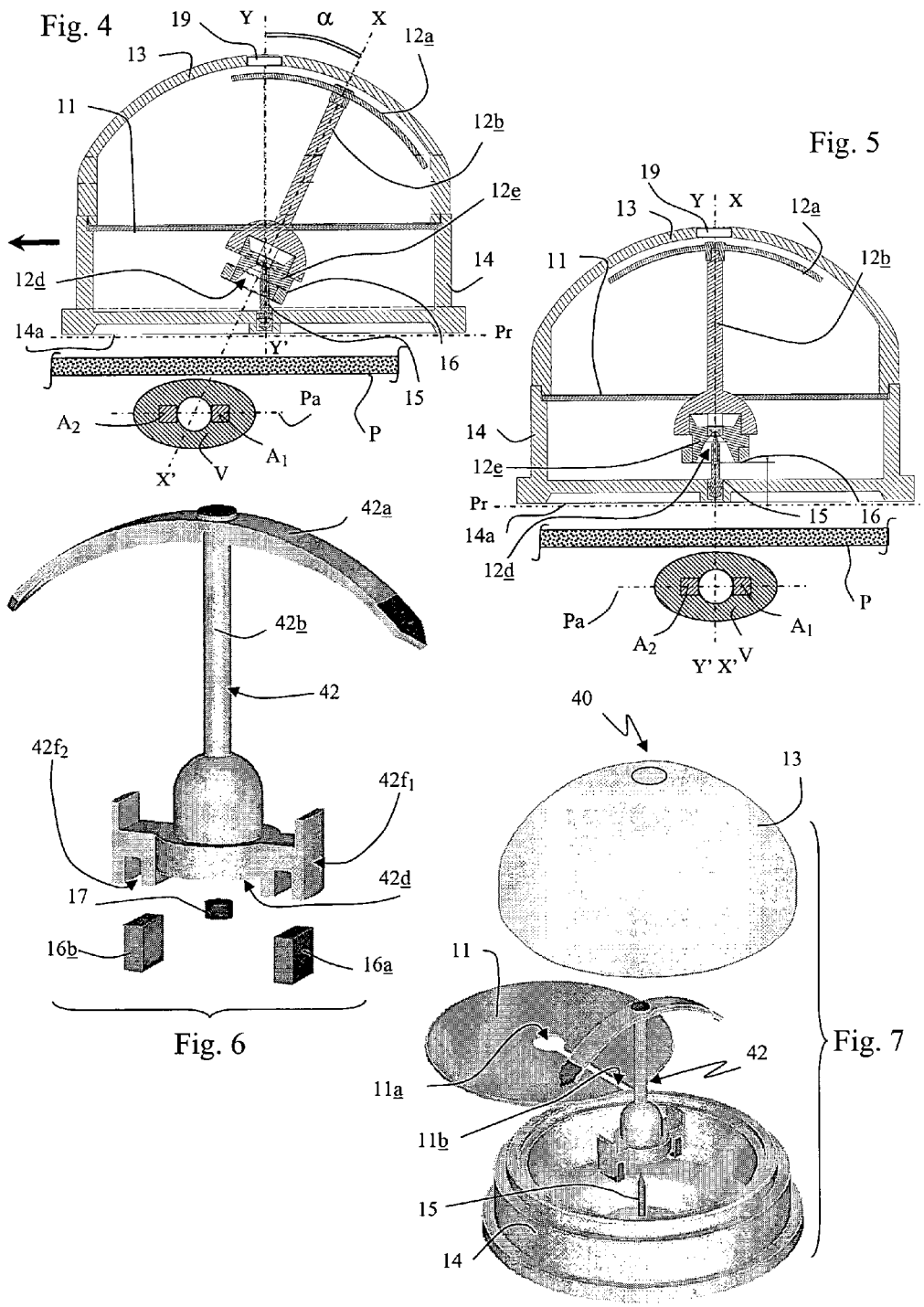

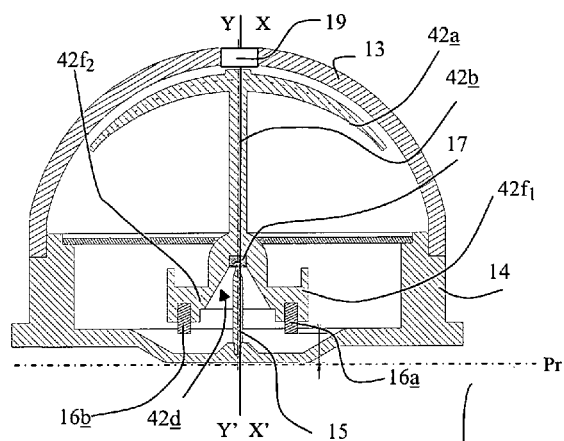
Fig. 8
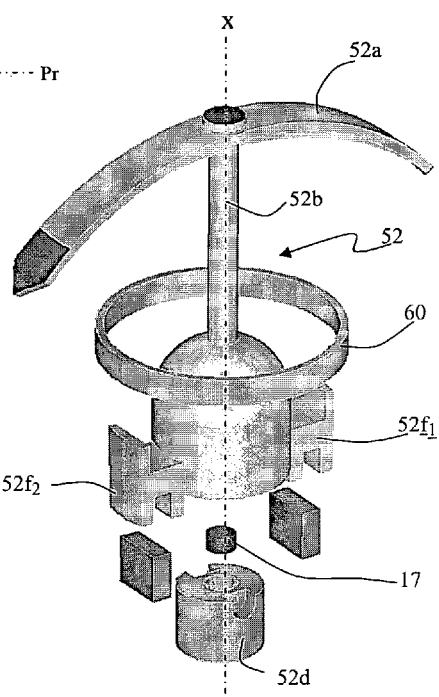
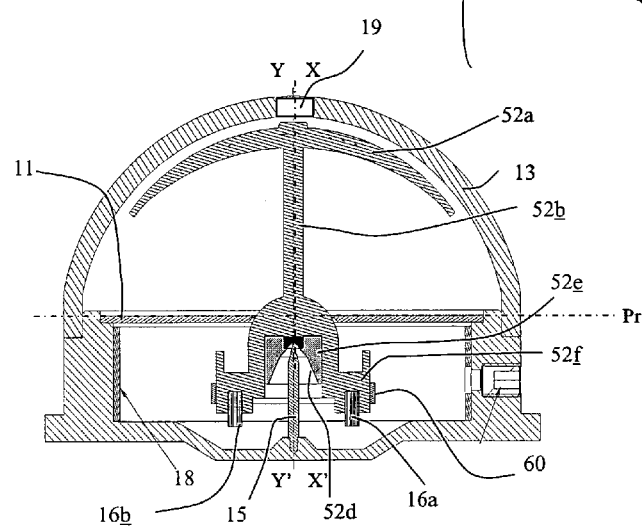
Fig. 9
Fig. 10

DEVICE AND METHOD FOR MECHANICALLY LOCATING AND READING THE SETTING OF AN ADJUSTABLE VALVE

The invention relates to a device and a method for locating and indicating the setting of an adjustable valve.

This type of valve is used in the field of medicine, for example, in the treatment of hydrocephalus.

This affliction is characterized by hypersecretion of cerebro-spinal fluid (CSF), insufficient resorption, or a mechanical obstruction of the passageways, thus leading to neurological and/or motor disorders in the patient.

This type of valve is well known to those skilled in the art who can, in particular, make reference to Patents EP 0 060 369 and EP 0 688 575 for examples of embodiments of such a valve.

One of the technical problems that this valve is able to solve is that of non-invasive adjustment of the valve setting. Indeed, while it is necessary to operate on the patient in order to implant drainage apparatus including the valve and catheters at the required location, it is important for the settings to be able to be adjusted after the operation in response to a positive or negative change in the disorder in order to drain more or less CSF from the cerebral ventricles or from the arachnoid space (cavum subarachnoidale).

In order to solve this problem, the valve settings can be adjusted by rotating a rotor equipped with magnetic elements. Using setting-adjustment apparatus also equipped with magnetic elements, it is possible to rotate the valve, through the patient's skin, using the magnetic coupling between the magnetic elements of the valve rotor and those of the setting-adjusting apparatus.

A first system of the prior art comprises an instrument for locating, an instrument for indicating the setting and an instrument for adjusting the setting of a valve implanted in a patient. These instruments are used in sequence. The location instrument is positioned over the valve once this valve has been found by palpating the patient's skin. The location instrument is then positioned on the skin over the valve so that the valve sits in an aperture of the location instrument. Finally, the instrument for indicating the setting of the valve is positioned over the centre of the valve thus identified. This second instrument comprises a magnetized needle able to pivot in a plane. This needle therefore follows the orientation of the magnetic elements of the valve and therefore indicates the setting. The third instrument, the one for adjusting the setting, is in turn positioned over the valve and manipulated in such a way as to allow a greater or lesser amount of CSF to pass. This device is not very practical because it is possible to confuse the valve with a subcutaneous reservoir or with a bony outgrowth without the location instrument flagging this error, the needle orientating itself along the earth's magnetic field in the absence of any other magnetic field. Furthermore, it is not very accurate because the aperture in the location instrument has, of necessity, to have dimensions large enough not to stretch the patient's skin to a dangerous extent that could injure it. Thus, the centre of the valve is identified only approximately which means that errors may arise in the reading of the setting. Finally, as the centre of the valve is identified only by inserting the valve in the aperture of the location instrument, it is not possible to locate then adjust the setting of a valve that is inaccessible or has been inserted more deeply.

Another system in the prior art consists of an indicator of the position and of the setting of a valve implanted in a patient, comprising a compass that allows the valve setting to be determined. This compass comprises an array of magnetic sensors and a signal processing device for processing the signal emitted by these sensors. These sensors measure the field strengths in order directly to detect the setting of the valve without going through a step of determining the magnetic centre, which step is needless in the type of valve depicted in this patent. Although it is accurate, this device is complicated to use because it entails computerized processing of the signal, and consequently, a source of electrical energy.

In order to remedy the disadvantages of the known solutions, the present invention proposes, using a magnetic indicator that can be positioned with respect to a reference plane, to identify the magnetic centre and the orientation of the valve in this reference plane when the device is superimposed on the valve.

To these ends, the subject of the invention is a device for mechanically locating and reading the setting of an adjustable magnetic valve for controlling the flow of a fluid in a predetermined direction, comprising a magnetic compass and a selector provided with an alignment mark for aligning the magnetic compass with respect to the direction in which the fluid flows through the valve, in which device the magnetic compass comprises a reference plane and a magnetic indicator which is mounted such that it can pivot in all three dimensions of space under the effect of the magnetic field of the valve, the valve setting being represented by the angle formed, in the reference plane, between the magnetic indicator and the alignment mark when the magnetic indicator is positioned perpendicular to the reference plane, the magnetic compass then being centred on the magnetic centre of the valve.

This device thus makes it possible, in a single step, to locate, with accuracy, the magnetic centre of the valve, determined by the position of the magnetic indicator perpendicular to the reference plane, and to identify the setting of the valve, as determined by the angular position of the magnetic indicator with respect to the direction indicated by the alignment mark.

According to other embodiments:
- the magnetic compass may have a detection means designed to determine whether the axis of the magnetic indicator is perpendicular to the reference plane;
- the control means may be a centering sight;
- the magnetic indicator may be designed to rest on a pivot allowing it to rotate in all three dimensions of space under the effect of the magnetic field of the valve;
- the magnetic indicator may have a pin surmounted by a setting-indicating element running substantially perpendicular to the pin, a part for resting on the pivot and a part for attaching at least one magnet able to receive a magnetic field;
- the attaching part may be disposed on the opposite side of the resting part to the setting-indicating element;
- the magnetic indicator may comprise a pivot-angle restrictor;
- the pivot-angle restrictor may be in the form of a hemispherical, hemiovoid or frustoconical swivel cage;
- a reinforcing means may be positioned in the resting part for the pivot;
- the reinforcing means may be made of a material chosen from ruby, corundum and a ceramic;
- a balancing ring may be positioned around the part for attaching the magnet coaxial with the pin and on the opposite side of the part for resting on the pivot to the setting-indicating element;
- the device may further comprise magnetic screening intended to protect the magnetic compass from an external magnetic field other than that of the valve;

the selector and the magnetic compass may be separable; and/or the selector may be equipped with a reading interface for reading the setting of the valve (V).

The invention also relates to an assembly for locating and indicating the setting of a magnetic valve, comprising a device as above together with a programmer able to emit a magnetic field strong enough to alter the setting of the valve.

The invention also relates to a method for mechanically locating and reading the setting of an adjustable magnetic valve for controlling the flow of a fluid with a device for indicating the setting of a valve as above, the method involving the steps consisting in:
a) orientating the selector in such a way that the alignment mark is aligned with the predetermined direction in which the fluid flows through the valve;
b) moving the said device over the valve, maintaining the alignment with respect to the direction in which the fluid flows through the valve,
c) immobilizing the said device when the magnetic indicator is positioned substantially perpendicular to the reference plane, then
d) identifying the angle formed, in the reference plane, between the magnetic indicator and the direction indicated by the alignment mark.

According to some other embodiments:
the method may further comprise a step e) which consists in reading on a reading interface a pressure value corresponding to the angle identified in step d);
the method may further comprise a step f) which consists in using an assembly as above, in replacing the magnetic compass with the programmer and in emitting a magnetic field strong enough to alter the setting of the valve; and/or
the method may further comprise a preliminary step which consists in initially locating the valve by palpation in an approximate region in which the valve is located.

Throughout this text, the centre of the valve must be understood to be the magnetic centre of the valve rather than its geometric centre.

The present invention can be used in any industrial or medical application in which an adjustable magnetic valve, intended to control the flow of a fluid, has been installed or implanted with a known direction in which the fluid flows, but in a way that is not directly accessible, for example under a panel that it is difficult to remove, or in the body of a patient. Only the latter medical application of the invention is described hereinafter, without this in any way meaning that the applicant is renouncing its rights in respect of industrial applications.

Other features of the invention will be listed in the detailed description given hereinbelow with reference to the attached drawings which, respectively, depict:

FIG. 1: a schematic perspective view of a device according to the invention for locating and indicating the setting of an adjustable-pressure magnetic valve, FIG. 2: an exploded perspective view of the magnetic compass of the device of FIG. 1;

FIG. 3: an exploded perspective view of the magnetic indicator of the magnetic compass of FIG. 2;

FIGS. 4 and 5: schematic sectioned views of the magnetic compass of FIG. 1, in use;

FIG. 6: an exploded perspective view of another embodiment of a magnetic indicator according to the invention;

FIG. 7: an exploded perspective view of a magnetic compass incorporating the magnetic indicator of FIG. 6;

FIG. 8: a schematic sectioned view of the magnetic compass of FIG. 7;

FIG. 9: an exploded perspective view of another embodiment of a magnetic indicator according to the invention; and FIG. 10: a schematic sectioned view of a magnetic compass equipped with the magnetic indicator of FIG. 9.

With reference to FIG. 1, a locating and setting-indicating device 100 according to the invention comprises a magnetic compass 10, and a selector 20 equipped with a reading interface 22 and with an alignment mark 21 for aligning the magnetic compass 10 with respect to the direction D in which the fluid flows through the valve. This direction D is known and predetermined at the time of implanting the valve (not depicted) in a patient. As will be specified hereinafter, it is preferable for the magnetic compass and the selector to be separable from one another so that a valve programmer can be fitted onto the selector in place of the magnetic compass once the magnetic centre has been identified and thus be used to adjust the valve setting because the programmer is located precisely over the centre of the valve.

More particularly, the magnetic compass 10 comprises a plate 11 preferably positioned parallel to a reference plane Pr (see FIG. 4) and a magnetic indicator 12 mounted in such a way that it can pivot in all three dimensions in space under the effect of a magnetic field.

In a first embodiment of such a magnetic compass, as illustrated by the exploded view in FIG. 2, the magnetic compass comprises a transparent dome 13 in the shape of a hemisphere and a baseplate 14 which are intended, together, to form a housing with a flat lower base 14a. The attached plate 11 is intended to be fixed to the baseplate 14 in or parallel to a reference plane Pr, and the magnetic indicator 12 comprises a setting-indicating element consisting of a needle 12a and of a pin 12b which is intended to be fixed perpendicular to the needle 12a.

In addition, the baseplate 14 is equipped with a pivot 15 the free end of which constitutes a point on which the pin 12b can rest, so that it can thus pivot in all three dimensions in space under the effect of a magnetic field.

FIG. 3 illustrates, in detail, the structure of the magnetic indicator 12. In this embodiment, the magnetic indicator 12 can be dismantled and is made up of several components.

Thus, the pin 12b comprises a means 12c of attachment to the needle 12a so that this needle surmounts the pin 12b, running substantially perpendicular to it.

The magnetic indicator 12 also comprises a part 12d for resting on the pivot 15, this part being situated on a component 12e intended to be attached to the pin 12b.

This resting part 12d is in the form of a frustoconical swivel cage allowing the pin 12b to pivot in space without becoming detached from the pivot 15. This shape can also limit the three-dimensional rotation of the magnetic indicator to an extent that is dependent on its cone angle.

Furthermore, the magnetic indicator 12 is equipped with a part 12f for the attachment of an annular magnet 16, this attachment also being situated on the component 12e. The attachment part 12f is disposed opposite the needle 12a with respect to the part 12d for resting, that is to say that it is on the opposite side of the pivot point to the needle.

Finally, a reinforcing means 17 is positioned in the bottom of the resting part 12d between the pin 12b and the pivot 15.

The purpose of this reinforcing means is to reinforce the pivot point, and therefore achieve highly accurate pivoting. It may be made of a component made of ruby, corundum, ceramic, etc. positioned in the bottom of the resting part 12d.

Upon assembly, the pin 12b is fed through an opening 11a in the plate 11, then the needle 12a is attached to the pin 12b via the attachment means 12c. The magnetic indicator is then placed on the pivot 15 and the plate 11 is positioned on the baseplate 14. Finally, the transparent dome 13 is attached to the baseplate.

The magnetic indicator 12 therefore rests on the pivot 15, allowing it to pivot in all three dimensions in space under the effect of a magnetic field. All that is then required is to choose an opening 11a that is wide enough to allow a predetermined maximum angular pivoting while at the same time being narrower than the component 12d so that the plate 11 acts as a guard rail to prevent the magnetic indicator from falling off the pivot 15. The way in which this location device works is illustrated in FIGS. 4 and 5.

To make it easier to detect the magnetic centre, the dome of the magnetic compass preferably has a detection means designed to determine whether the axis X-X' of the magnetic indicator is perpendicular to the reference plane Pr. In the embodiment illustrated, this means is a centering sight 19 positioned in such a way that the axis X-X' of the magnetic indicator is in concordance with the axis Y-Y' of the magnetic compass, perpendicular to the reference plane Pr, when the magnetic compass is superimposed on the valve and the magnetic indicator is situated precisely over the centre of the valve.

As illustrated in FIGS. 4 and 5, the user orientates the selector 20 of the device 100 according to the invention in such a way that the alignment mark 21 is aligned with the direction D in which the fluid flows through the valve. This direction D is determined at the time of implantation of the valve and remains constant throughout the patient's life. The user also holds the device in such a way that the reference plane Pr is parallel to the plane Pa formed by the magnets of the valve. The plane Pa is known and predetermined during implantation of the valve which, in general, is implanted in such a way that the plane Pa runs substantially parallel to the surface of the skin, with an acceptable trim error of a few degrees which may, for example, represent plus or minus 5°. It is therefore desirable for the device to be equipped with a means of positioning with respect to the plane Pa. For example, the underside 14a of the housing 14 may be disposed parallel to the plane Pr so that all the user has to do is to position the device in such a way that the underside 14a is pressed against the patient's skin.

The user then moves the magnetic compass/selector assembly over the valve, on the one hand maintaining the alignment of the device with respect to the direction (D) in which the fluid flows through the valve and, on the other hand, keeping the reference plane Pr parallel to the plane Pa.

The user then immobilizes the magnetic compass/selector assembly when the magnetic indicator 12 is positioned substantially perpendicular to the reference plane Pr, that is to say when the user notices that the axis of the magnetic indicator 12 is positioned within the sight 19.

What happens is that the annular magnet 16 of the magnetic indicator 12 aligns itself with the magnetic field generated by the magnets $A_1$-$A_2$ of the valve V, thus rotating the magnetic indicator about the pivot point. Thus, for all the time that the magnetic indicator 12 is not precisely superimposed on the magnetic centre of the valve V, it makes an angle a with the perpendicular to the reference plane Pr.

When the magnetic indicator 12 is positioned perpendicular to the reference plane Pr passing through the underside 14a (FIGS. 5 and 10), that means that it is superimposed on the magnetic axis of the valve V, which means that the location of the magnetic centre of the valve V is known accurately through the skin P.

There is therefore no need to have located the valve by palpation beforehand in order to be able to locate its magnetic centre because the magnetic compass itself indicates the direction to follow. As a result, deeply implanted valves can be identified using the device according to the invention. However, if the situation lends itself to such an approach, that is to say when the valve is subcutaneous, and in order to save time, the user may initially locate the valve V by palpation in the approximate region in which the valve V is located before aligning the selector with the direction of flow D.

The valve setting is then represented by the angle β formed, in the reference plane, between the magnetic indicator 12 and the direction D indicated by the alignment mark (FIG. 1), that is to say by the angle β formed between the orthogonal projection of the needle 12a onto the reference plane Pr and the direction D. Thus, as illustrated in FIG. 1, it is possible on the interface 22 to read that the valve has been set to allow fluid to pass when the pressure is 110 mm $H_2O$ (namely about 1078.73 Pa) or higher.

The device can be contained in an assembly also equipped with a magnetic field emitter, known as a programmer, able to emit a magnetic field strong enough to alter the setting of the valve. In such a case, having accurately located the magnetic centre of the valve and the valve setting, the user commands the emission of a magnetic field strong enough to alter the setting of the valve. To do that, in the preferred embodiment in which the selector and the magnetic compass are separable, the user holds the selector 20 at the precise location where the magnetic centre of the valve has been located, removes the magnetic compass 10 from the selector 20 and replaces it) with a programmer able to fit inside the selector 20. The user can then alter the setting appropriately according to the desired pressure setting for the valve.

FIGS. 7 and 8 illustrate another embodiment of a magnetic compass 40 of a device for locating and indicating the setting of a magnetic valve according to the invention. In this embodiment, the magnetic indicator consists of a single component 42 having a part 42a forming a needle that indicates the setting, a part 42b forming a pin, a part 42d (FIG. 8) for resting, and a part $42f_1$-$42f_2$ for attaching two magnets 16a and 16b. A pivot reinforcing ruby 17 may also be positioned at the interface between the pivot 15 and the part 42d.

To assemble this magnetic compass (FIG. 7) it is necessary to choose a plate 11 that has a cut-out 11b to allow the pin 42b to be inserted into the opening 11a.

The other steps in the assembly are identical to that of the embodiment of FIG. 2.

FIG. 9 illustrates another embodiment combining the aforementioned two embodiments, namely a one-piece magnetic indicator 52 comprising a needle 52a, a pin 52b, a resting part 52d located on an attachment component 52e, and a part $52f_1$-$52f_2$ for attaching the magnets 16a, 16b.

The purpose of the part 52e is to limit the maximum angle of pivoting of the magnetic indicator while at the same time limiting the amount of ruby to be used only at the pin/pivot contact point.

Furthermore, the magnetic indicator comprises a balancing ring 60 improving the balance of the magnetic indicator 52 by counterbalancing the weight of the attachment parts $52f_1$ and $52f_2$ between these attachment parts.

This balancing ring 60 is positioned around the part $52f_1$-$52f_2$ for attaching the magnet, coaxial with the pin 52b and on the opposite side of the part 52d for resting on the pivot 15 to the setting-indicating element 52a.

Furthermore, magnetic screening 18 intended to protect the magnetic compass from an external magnetic field other than that of the valve is positioned around the magnetic indicator 52 and more specifically around the magnets 16a-16b.

This screening can also be used in the aforementioned embodiments.

Numerous variations and alternatives may be adopted without thereby departing from the invention. In particular:
- the compass can be used to determine the setting of any type of adjustable magnetic valve, such as the aforementioned adjustable-pressure valves or adjustable-flow magnetic valves in which the valve closes when a determined amount of fluid, calculated as a function of the time for which the valve has been open and of the set throughput, has passed through the valve,
- instead of being mounted resting on a rotation pivot, the magnetic indicator may be mounted on a swivel or on three respectively perpendicular pivot pins, so that the indicator can position itself in all three dimensions in space;
- the reference plane may consist of the base of the baseplate 14 rather than of an attached plate 11;
- the detection means may be a sensor emitting an audible signal when the axis of the magnetic indicator is perpendicular to the reference plane;
- the pivot-angle restrictor may have the form of a hemispherical or hemiovoid swivel cage;
- the magnet may be annular or may consist of two magnets;
- the plate may be graduated to make it easier to read the valve setting;
- the reading interface 22 has as many setting-indicating marks 22a as the valve has setting positions. Thus, in FIG. 1, the reading interface is designed for a valve with up to five setting positions. For a valve with, for example twenty-four setting positions, the interface will have at least twenty-four marks 22a;
- the magnetic indicator may comprise a visual means 23 of indicating the mark 22a that corresponds to the valve setting position. This mark may be a simple symbol such as an arrow, a coloured mark or a line, but may equally be embodied by a particular shape of the magnetic indicator. This visual means is especially useful when the marks 22a are diametrically opposed on the reading interface 22 because it makes it possible, from two opposed marks 22a, to determine unambiguously which is the one that corresponds to the valve setting position.

The invention claimed is:

1. A device for mechanically locating and reading the setting of an adjustable magnetic valve (v) for controlling the flow of a fluid in a predetermined direction (D), comprising a magnetic compass (10) and a selector (20) provided with an alignment mark (21) for aligning the magnetic compass (10) with respect to the direction (D) in which the fluid flows through the valve (V), characterized in that the magnetic compass (10) comprises a reference plane (Pr) and a magnetic indicator (12, 42, 52) which is mounted such that it can pivot in all three dimensions of space under the effect of the magnetic field of the valve, the valve setting being represented by the angle (β) formed, in the reference plane, between the magnetic indicator (12, 42, 52) and the alignment mark (21) when the magnetic indicator (12, 42, 52) is positioned perpendicular to the reference plane (Pr), the magnetic compass then being centered on the magnetic centre of the valve.

2. A device according to claim 1, in which the magnetic compass has a detection means designed to determine whether the axis (X-X') of the magnetic indicator is perpendicular to the reference plane (Pr).

3. A device according to claim 2, in which a control means is a centering sight (19).

4. A device according to claim 1, in which the magnetic indicator (12, 42, 52) is designed to rest on a pivot (15) allowing it to rotate in all three dimensions of space under the effect of the magnetic field of the valve.

5. A device according to claim 4, in which the magnetic indicator (12, 42, 52) has a pin (12b, 42b, 52b) surmounted by a setting-indicating element (12a, 42a, 52a) running substantially perpendicular to the pin (12b, 42b, 52b), a part (12d, 42d, 52d) for resting on the pivot and a part (12f, 42f1-42f2, 52f) for attaching at least one magnet (16, 16a, 16b) able to receive a magnetic field.

6. A device according to claim 5, in which the attaching part (12f, 42f1-42f2, 52f) is disposed on the opposite side of the resting part (12d, 42d, 52d) to the setting-indicating element (12a, 42a, 52a).

7. A device according to claim 1, in which the magnetic indicator (12, 42, 52) comprises a pivot-angle restrictor (12e, 52e).

8. A device according to claim 7, in which the pivot-angle restrictor is in the form of a hemispherical, hemiovoid or frustoconical swivel cage.

9. A device according to claim 5, in which a reinforcing means (17) is positioned in the resting part (12d, 42d, 52d) for the pivot (15).

10. A device according to claim 9, in which the reinforcing means (17) is made of a material chosen from ruby, corundum and a ceramic.

11. A device according to claim 5, in which a balancing ring (60) is positioned around the part (12f, 42f1-42f2, 52f) for attaching the magnet (16, 16a, 16b) coaxial with the pin (12b, 42b, 52b) and on the opposite side of the part (12d, 42d, 52d) for resting on the pivot (15) to the setting-indicating element (12a, 42a, 52a).

12. A device according to claim 1, further comprising magnetic screening (18) intended to protect the magnetic compass from an external magnetic field other than that of the valve.

13. A device according to claim 1, in which the selector (20) and the magnetic compass (10) are separable.

14. A device according to claim 1, in which the selector (20) is equipped with a reading interface (22) for reading the setting of the valve (V).

15. An assembly for mechanically locating and reading the setting of an adjustable magnetic valve (V), comprising a device according to claim 1 together with a programmer able to emit a magnetic field strong enough to alter the setting of the valve.

16. A method for mechanically locating and reading the setting of an adjustable magnetic valve for controlling the flow of a fluid with a device for indicating the setting of a valve according to claim 1, characterized in that it involves the steps consisting in:
   a) orientating the selector (20) in such a way that the alignment mark (21) is aligned with the predetermined direction (D) in which the fluid flows through the valve;
   b) moving the said device over the valve, maintaining the alignment with respect to the direction (D) in which the fluid flows through the valve,
   c) immobilizing the said device when the magnetic indicator (12, 42, 52) is positioned substantially perpendicular to the reference plane (Pr), then
   d) identifying the angle (β) formed, in the reference plane, between the magnetic indicator (12, 42, 52) and the direction (D) indicated by the alignment mark (21).

17. A method according to claim 16, further comprising a step e) which consists in reading on a reading interface (22) a pressure value corresponding to the angle (β) identified in step d).

18. A method according to claim 16, further comprising a step f) which consists, in replacing the magnetic compass with a programmer able to emit a magnetic field strong enough to alter a setting of the valve and emitting a magnetic field strong enough to alter the setting of the valve.

19. A method according to claim 16, further comprising a preliminary step which consists in initially locating the valve (V) by palpation in an approximate region in which the valve is located.

* * * * *